(12) United States Patent
Férin et al.

(10) Patent No.: US 12,329,576 B2
(45) Date of Patent: Jun. 17, 2025

(54) FLEXIBLE PRINTED CIRCUIT BOARD DEVICE FOR INTERFACING HIGH DENSITY ULTRASOUND MATRIX ARRAY TRANSDUCER WITH INTEGRATED CIRCUITS

(71) Applicant: VERMON S.A., Tours (FR)

(72) Inventors: Guillaume Férin, Truyes (FR); Philippe Vince, Truyes (FR)

(73) Assignee: VERMON SA, Tours (FR)

( * ) Notice: Subject to any disclaimer, the term of this patent is extended or adjusted under 35 U.S.C. 154(b) by 0 days.

(21) Appl. No.: 17/430,788

(22) PCT Filed: Feb. 21, 2020

(86) PCT No.: PCT/IB2020/051481
§ 371 (c)(1),
(2) Date: Aug. 13, 2021

(87) PCT Pub. No.: WO2020/170210
PCT Pub. Date: Aug. 27, 2020

(65) Prior Publication Data
US 2022/0125408 A1    Apr. 28, 2022

Related U.S. Application Data

(60) Provisional application No. 62/809,193, filed on Feb. 22, 2019.

(51) Int. Cl.
*A61B 8/00* (2006.01)
*H05K 1/02* (2006.01)

(52) U.S. Cl.
CPC .......... *A61B 8/4483* (2013.01); *A61B 8/4477* (2013.01); *H05K 1/028* (2013.01)

(58) Field of Classification Search
CPC ... A61B 8/4483; A61B 8/4477; A61B 8/4488; A61B 8/4494; B06B 1/0629;
(Continued)

(56) References Cited

U.S. PATENT DOCUMENTS 5,160,269 A * 11/1992 Fox, Jr. .................. H01R 12/78
439/67
2001/0006252 A1    7/2001 Kim et al.
(Continued)

FOREIGN PATENT DOCUMENTS

JP    2006-110140 A    4/2006
JP    2018-148109 A    9/2018

OTHER PUBLICATIONS

The National Intellectual Property Administration, PRC, Notification of the First Office Action issued In corresponding Application No. 202080016254.6, issued Jun. 30, 2022.
(Continued)

*Primary Examiner* — Joseph M Santos Rodriguez
*Assistant Examiner* — Zainab Mohammed Aldarraji
(74) *Attorney, Agent, or Firm* — Stites & Harbison, PLLC; Jeffrey A. Haeberlin; James R. Hayne

(57) ABSTRACT

A flexible printed circuit board includes a central portion and one or more tabs extending from the central portion. The one or more tabs are foldable relative to the central portion. A plurality of pads are located within the central portion, and the plurality of pads are configured to electrically connect to a transducer. Lands are located within one of the one or more tabs, and electrical traces connect the plurality of pads and the lands. A method of manufacturing an electronics assembly includes providing a flexible printed circuit board with a plurality of central portions and folding the substrate such that the adjacent central portions are vertically stacked and the pads of adjacent central portions are electrically con-
(Continued)

nected. Prior to folding the substrate, a transducer may be affixed to the plurality of pads and one or more electrical components may be affixed to the lands.

21 Claims, 11 Drawing Sheets

(58) Field of Classification Search
CPC ........ H05K 3/363; H05K 1/118; H05K 1/028; H05K 1/144; H05K 1/189; H05K 2201/0397; H05K 2201/041; H05K 2201/052; H05K 2201/055; H05K 2201/058; H05K 2201/09227; H05K 2201/09445; H05K 2201/10151; H05K 2203/167
See application file for complete search history.

(56) References Cited

U.S. PATENT DOCUMENTS

| | | |
|---|---|---|
| 2002/0114143 A1 | 8/2002 | Morrison et al. |
| 2005/0184376 A1* | 8/2005 | Salmon ............... H01L 23/5386 257/E21.526 |
| 2005/0221633 A1* | 10/2005 | Wildes ................... H05K 3/365 439/67 |
| 2007/0244392 A1* | 10/2007 | Tezuka .................. B06B 1/0629 600/459 |
| 2008/0178677 A1 | 7/2008 | Baumgartner et al. |
| 2016/0007964 A1* | 1/2016 | Ona ..................... A61B 8/4494 600/459 |
| 2018/0261577 A1* | 9/2018 | Otsuka .................. H01L 25/105 |

OTHER PUBLICATIONS

European Patent Office, International Search Report issued in corresponding Application No. PCT/IB2020/051481 mailed Jul. 24, 2020.
Japan Patent Office, Office Action (Notice of Reasons for Refusal) issued in corresponding Application No. JP 2021-549345, mailed Oct. 3, 2023. (Partial Translation).
European Patent Office, Examination Report issued in corresponding Application No. EP 20709730, mailed Sep. 12, 2023.
European Patent Office, Examination Report issued in corresponding Application No. EP 20709730.4 dated Apr. 3, 2025.

* cited by examiner

FLEXIBLE PRINTED CIRCUIT BOARD DEVICE FOR INTERFACING HIGH DENSITY ULTRASOUND MATRIX ARRAY TRANSDUCER WITH INTEGRATED CIRCUITS

RELATED APPLICATIONS

This application claims the benefit of U.S. Provisional Application No. 62/809,193, filed Feb. 22, 2019, the entire disclosure of which is incorporated herein by this reference.

FIELD OF THE INVENTION

The presently disclosed subject matter relates to an ultrasound matrix array transducer with embedded integrated circuits (ICs) for cable count reduction, system simplification, and digital systems in medical imaging and therapy and ultrasound non-destructive testing (NDT) fields.

BACKGROUND OF THE INVENTION

Current ultrasound matrix arrays exhibit several thousands of very small individual elements to achieve volumetric imaging. Each of these elements needs to individually be analogically driven by electronics (e.g., analog front-end ("AFE")). However, an imaging system for such an ultrasound matrix array would be too expensive and the system complexity would be much too high. Further, cabling for such a system requires thousands of wires, and therefore is too big and too heavy for practical use.

So imaging system manufacturers have developed several strategies to reduce the number of independent electronic channels. Some of these strategies include: micro-beam formation, time domain multiplexing, and multiplexing. These strategies exhibit a reduction factor between 1:9 and 1:64, and even more. All of these techniques rely on integrating ICs close to the active ultrasound matrix array (e.g., in a probe housing the ultrasound matrix array). The ultrasound matrix array can be either a bulk piezoelectric component, or a capacitive or piezoelectric silicon-based micromachined transducer (CMUT or PMUT). One or more ICs are required to dramatically decrease the number of connections and independent channels.

One existing solution is based on direct IC attachment to the matrix transducer through a vertical architecture in which one or several application-specific integrated circuits (ASIC) are attached to each other and connected with wire bonding technologies and finally the acoustic module is flip-chipped onto the topmost IC. The interconnection module offers several advantages since the ICs are not required to exhibit the same footprint and element arrangement as the acoustic module. Thus, one or several ICs could be used for every probe topology without having to develop an ASIC for each topology. However, there are some limitations since current technologies do not allow interconnection at fine pitches (below 200 μm) and of large arrays (over 60×60) unless adding several layers of conductor tracks, thus dramatically reducing the flexibility of such printed circuits. With respect to this first strategy, it is noted that each transducer (i.e., acoustic module) configuration (i.e., arrangement of elements and pitch) requires a different, specific IC. The development of the IC is very expensive and it is absolutely not reconfigurable.

Another existing solution uses an interconnection module in which the module can be a foldable flexible printed circuit or a solid interposer which interface each element of the acoustic modules to the deported ICs. Of note, this second strategy is still a vertical integration. With respect to the interposer of this second strategy, some have attempted to solve the configurability issue by inserting an interposer material which adapts the pitch or even deports the interconnection, but at the expense of interconnection module complexity.

Lastly, some teams have proposed modular approaches where multiple acoustic modules are aligned and assembled together to overcome flex limitations. The whole system is mechanically aligned, but with possible uncertainty on element positions in translation and rotation that are unacceptable with regards to beam formation. This is a horizontal integration but the number of elements that are addressable is smaller and works for normal pitches.

BRIEF SUMMARY OF THE INVENTION

The presently disclosed subject matter relates to an ultrasound matrix array transducer with embedded integrated circuits (ICs) for cable count reduction, system simplification, and digital systems in medical imaging and therapy and ultrasound non-destructive testing (NDT) fields.

In some embodiments of the present invention, a flexible printed circuit board includes a central portion and one or more tabs extending from the central portion. The one or more tabs are foldable relative to the central portion. According to some embodiments, the one or more tabs extend from a periphery of the central portion. A plurality of pads are located within the central portion, and the plurality of pads are configured to electrically connect to a transducer. Lands are located within at least one of the one or more tabs, and electrical traces connect the plurality of pads and the lands.

In some embodiments, the flexible printed circuit board further includes a connector affixed to the lands. The connector is configured to electronically communicate with imaging equipment, including, for example, an external system with imaging equipment, displays, user controls, and the like.

In some embodiments, the flexible printed circuit board further includes an integrated circuit affixed to the lands. The integrated circuit is configured to control one or more elements of the transducer. Inclusion of the integrated circuits therefore provides a significant decrease in the number of connections to an external system.

In some embodiments, the flexible printed circuit board further includes a plurality of second surface pads located within the central portion on a side opposite from the plurality of pads with the plurality of second surface pads configured to electrically connect to another flexible printed circuit board. Vias extend through central portion with each via electrically connecting one the plurality of pads to one of the plurality of second surface pads. That is to say, vias connect the pads on a first side (i.e., first surface pads) to pads on a second side (i.e., second surface pads).

In some embodiments of the flexible printed circuit the one or more tabs define alignment holes extending through tabs.

In some embodiments, the flexible printed circuit board includes a plurality of central portions and hinge portions extend between adjacent central portions. According to this embodiment, each hinge portion is foldable such that, upon folding the flexible printed circuit board at the hinge portions, adjacent central portions can be vertically stacked. In some embodiments of the flexible printed circuit including hinge portions, the hinge portions define alignment holes extending through the hinge portions. The alignment holes defined within the hinge portions are used to ensure proper alignment of the central portions.

In some embodiments, the flexible printed circuit board includes a plurality of central portions and the one or more tabs extend between adjacent central portions. According to this embodiment, each of the one or more tabs are foldable such that, upon folding the flexible printed circuit board at the tabs, adjacent central portions can be positioned immediately adjacent to each other within the same plane. The pads of adjacent central portions then collectively connect to a high density ultrasound matrix array transducer.

In some embodiments of the flexible printed circuit the plurality of pads have a pitch of between about 20 μm to about 500 μm.

In some embodiments of the flexible printed circuit at least 1024 pads are located within the central portion.

In some other embodiments of the present invention, an ultrasonic probe includes a high density ultrasound matrix array transducer and a plurality of stacked circuit boards. Each circuit board includes a substrate having a first surface and a second surface opposite the first surface. The substrate includes a central portion and one or more tabs extending from the central portion with the one or more tabs foldable relative to the central portion. A plurality of first surface pads are positioned on the first surface of the substrate with each first surface pad located within the central portion of the substrate. A plurality of second surface pads are positioned on the second surface of the substrate with each second surface pad located within the central portion of the substrate. Vias extend through the substrate with each via electrically connecting one the plurality of first surface pads to one of the plurality of second surface pads. Lands are positioned on the first surface of the substrate with each land located within one of the one or more tabs of the substrate. Electrical traces electrically connect the lands to one or more of the plurality of first surface pads, one or more of the plurality of second surface pads, or both one or more of the plurality of first surface pads and one or more of the plurality of second surface pads. One or more integrated circuits are also affixed to the lands of at least one of the plurality of stacked circuit boards. The plurality of first surface pads of an upper circuit board are each electrically connected to one of the transducers of the high density ultrasound matrix array transducer, and the plurality of stacked circuit boards are electrically connected by way of the plurality of first surface pads and the plurality of second surface pads such that each of the transducers of the high density ultrasound matrix array transducer is electrically connected to at least one of the one or more integrated circuits.

The present invention is also directed to a method of manufacturing an electronics assembly. In some exemplary implementations of the method a flexible folding substrate is first provided with the flexible folding substrate having a first surface and a second surface opposite the first surface. The substrate includes a plurality of central portions, hinge portions extending between adjacent central portions, and one or more tabs extending from each of the central portions. A plurality of pads are positioned on the first surface of the substrate and on the second surface of the substrate, with each pad located within one of the plurality of central portions of the substrate. Vias extend through the substrate and electrically connecting one the plurality of the pads on the first surface of the substrate to one of the plurality of pads on the second surface of the substrate. Lands are positioned on the first surface of the substrate with each land located within one of the one or more tabs of the substrate. Electrical traces connect the plurality of pads and the lands. According to some exemplary implementations of the method, the substrate is then folded at each hinge portion such that the adjacent central portions are vertically stacked and the pads of adjacent central portions are electrically connected. Each of the tabs are also folded relative to the central portion.

According to some exemplary implementations of the method, a transducer is also affixed to the plurality of pads positioned on the first surface of the substrate such that the transducer is affixed to an uppermost central portion after the substrate is folded at each hinge portion. According to some exemplary implementations the transducer is affixed to the plurality of pads prior to folding the substrate. In some particular implementations, the step of affixing the transducer comprises electrically connecting each element of a high density ultrasound matrix array transducer to a corresponding one of the plurality of pads positioned on the first surface of the substrate located within the uppermost central portion.

According to some exemplary implementations of the method, one or more integrated circuits are also affixed to the lands. According to some exemplary implementations the one or more integrated circuits are affixed to the lands prior to folding the substrate.

According to some exemplary implementations of the method the hinge portions define alignment holes extending through the substrate and the step of folding the substrate at each hinge portion includes aligning each of the alignment holes.

According to some exemplary implementations of the method the one or more tabs define alignment holes extending through the substrate and the step of folding each of the tabs includes aligning each of the alignment holes.

According to some exemplary implementations of the method an electrically conductive connective material is applied to the pads prior to folding the substrate. According to some exemplary implementations the electrically conductive connective material is solder and the method further comprises a step of heating the flex folding substrate to reflow the solder. In some other exemplary implementations the electrically conductive connective material is an anisotropic conductive film and the method further comprises a step of applying pressure to the vertically stacked central portions.

According to some exemplary implementations of the method the hinge portions are cut away from the central portions after the pads of adjacent central portions are electrically connected.

BRIEF DESCRIPTION OF THE DRAWINGS

Embodiment herein will hereinafter be described in conjunction with the appended drawings and illustrations provided to illustrate and not limit the scope of the claims:

FIG. 2B is a detailed view of the pads formed in the central portions of the first unit of the flexible substrate of FIGS. 1 and 2;

DETAILED DESCRIPTION OF EXEMPLARY EMBODIMENTS OF THE INVENTION

The present invention is directed to a flexible printed circuit board which allows for interfacing a high density ultrasound matrix array with integrated circuits (ICs).

Figure 5:
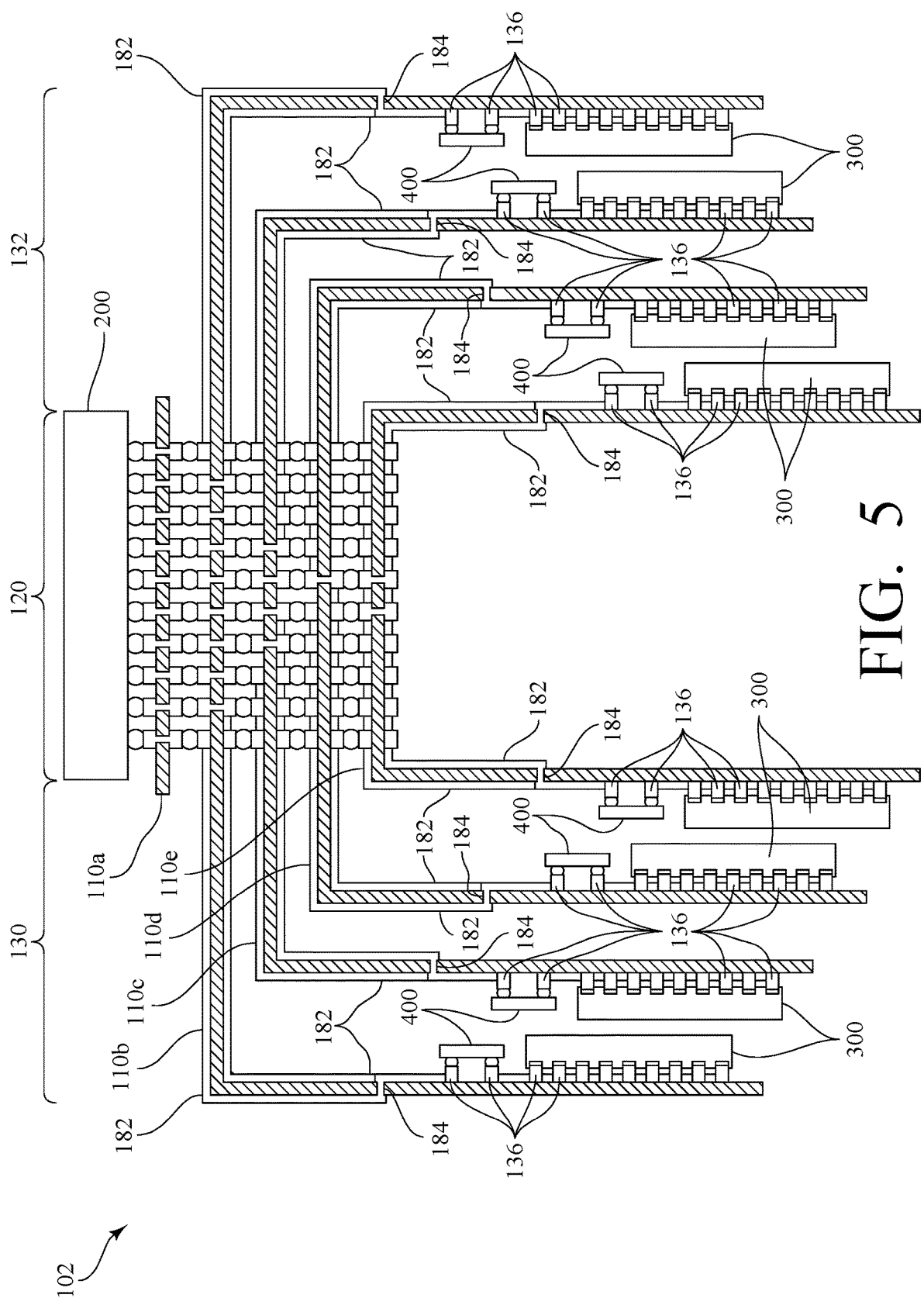
FIG. 5 is a cross-sectional view of an electronics assembly made in accordance with the first embodiment of the present invention.
Figure 6:
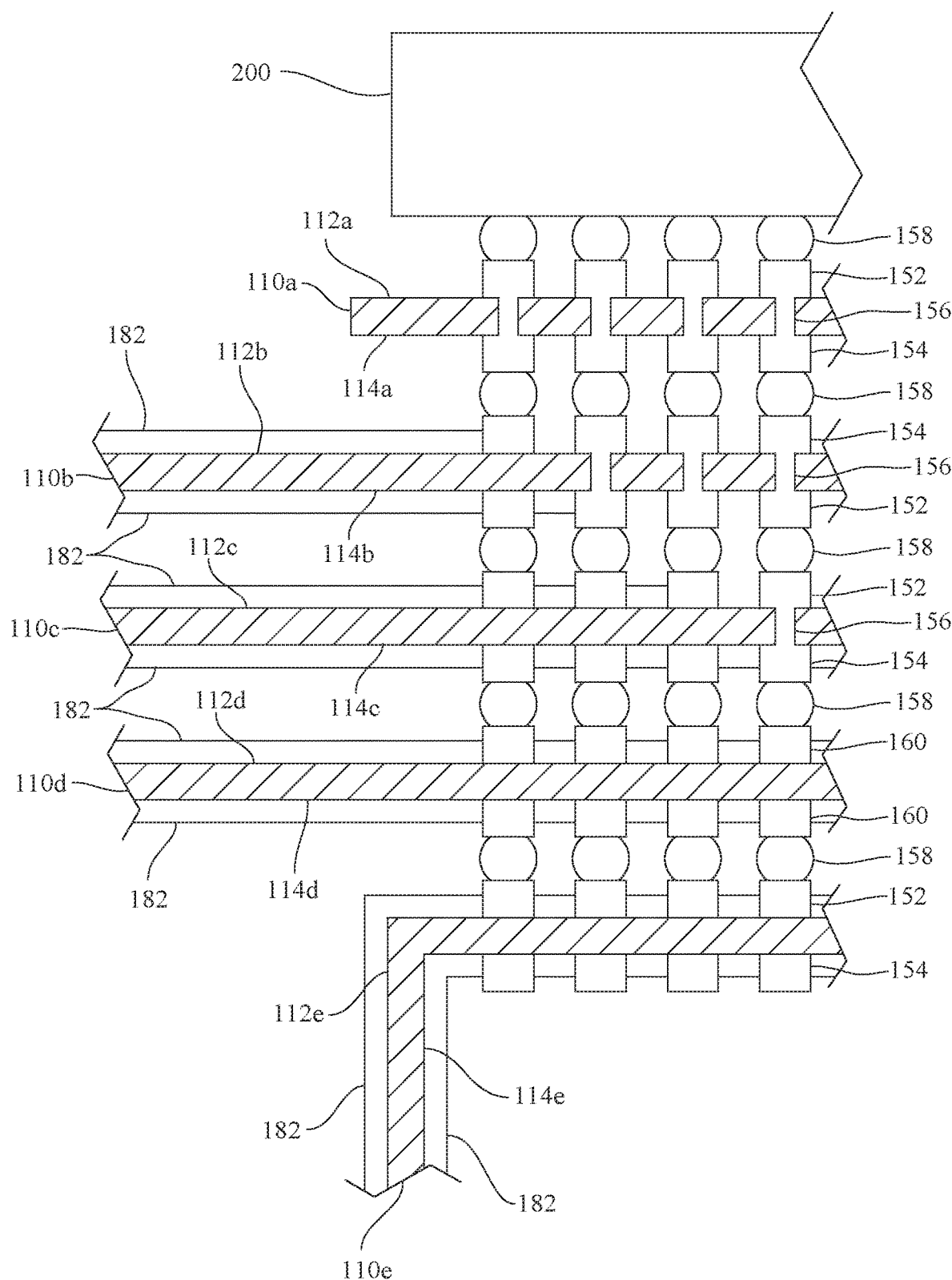
FIG. 6 is a detailed view of the vertically stacked circuit boards of FIG. 5.
Figure 7:
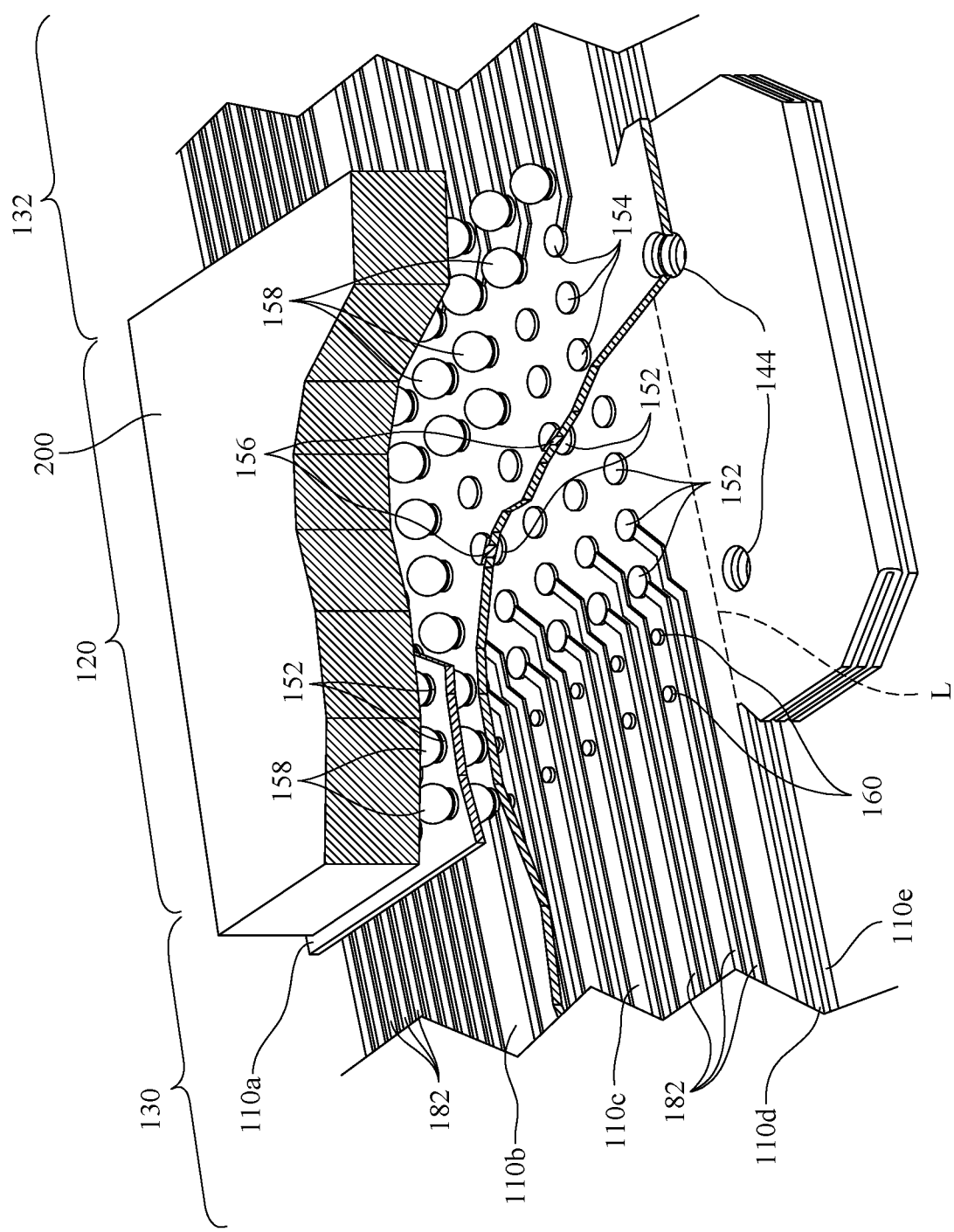
FIG. 7 is a partial cutaway of a perspective view of the electronics assembly of FIG. 5.

Referring first to FIGS. 5-7, a multi-layer electronics assembly 102 made in accordance with the present invention, and which is configured to be enclosed within a housing of an ultrasonic probe, includes a multi-layer stack of circuit boards 110a-110e which operably connect a high density ultrasound matrix array transducer (transducer 200) to imaging equipment. The stacked circuit boards 110a-110e are formed from a flexible circuit board which is configured to fold such that the central portion 120 of each of the circuit boards 110a-110e are vertically stacked and peripheral tabs 130, 132 are folded relative to the respective central portion 120. The transducer 200 is electrically connected to the central portion 120 of an uppermost circuit board 110a, but all of the central portions 120 are electrically connected to one another through a combination of pads 152, 154, vias 156, and solder balls 158, as perhaps best shown in FIG. 6 and discussed further below. Electrical traces 182 extend from each central portion 120 of the subsequent circuit boards 110b-110e along respective tabs 130, 132 where additional electronic components 300, 400 are affixed to the circuit boards 110b-110e by lands 136, as perhaps best shown in FIG. 5 and discussed further below. The architecture of the electronics assembly 102 thereby provides multiple locations for integrated circuits, or other electronic components to be connected, while maintaining an overall small footprint of the electronics assembly 102 in comparison to the size of the transducer 200. Further details and advantages of the present system will now be discussed.

Figure 1:
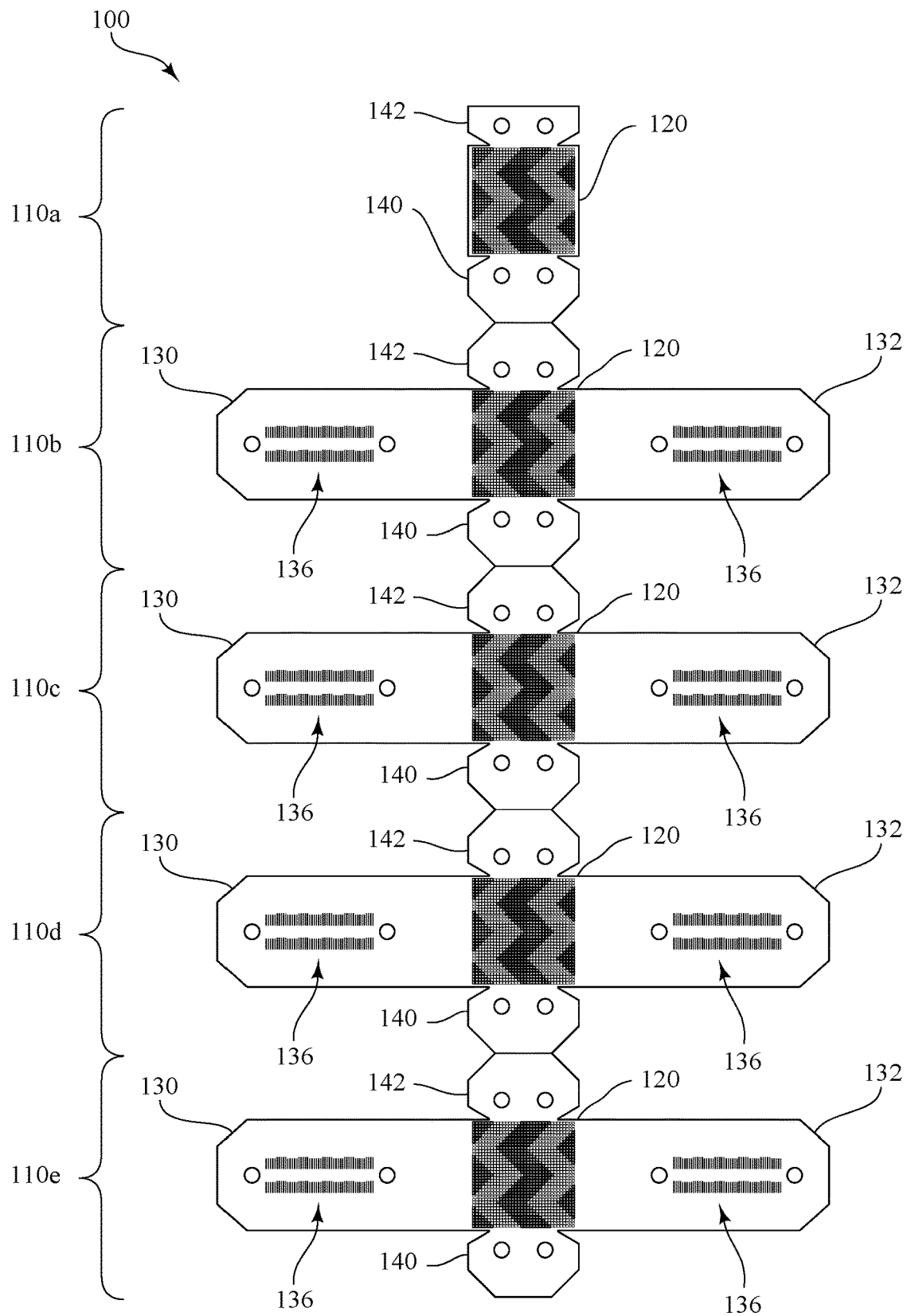
FIG. 1 is a plan view of a flexible substrate made in accordance with a first embodiment of the present invention.

Referring now to FIG. 1, in one exemplary embodiment of the present invention, a flexible printed circuit board (substrate 100) includes a plurality of units 110a-110e which are connected together. Each of these units 110a-110e later forms one of the stacked circuit boards 110a-110e shown in FIGS. 5-7. In particular, as discussed in detail below, in accordance with exemplary implementations of the method of the present invention, various electronic components are first attached to this flexible substrate 100 and the substrate 100 is then folded to arrive at the electronics assembly 102 shown in FIG. 5.

In the exemplary substrate 100 shown in FIG. 1, there are five units 110a-110e, but other numbers of units are contemplated without departing from the spirit and scope of the present invention. Regardless of the number of units, however, each unit includes a central portion 120 with each of the central portions 120 connected by hinge portions 140, 142, as discussed further below. Furthermore, the secondary units 110b-110e (i.e., all but the first unit 110a) each include tabs 130, 132 which extend away from the central portion 120 in opposite directions from a periphery of the central portion 120, but other configurations are possible. For example, in some alternate embodiments a first unit could include one or more tabs and each of the secondary units could include zero, one, or two tabs. The particular number and placement of the tabs are chosen based on the desired configuration of the resulting multi-layer electronics assembly.

Figure 2:
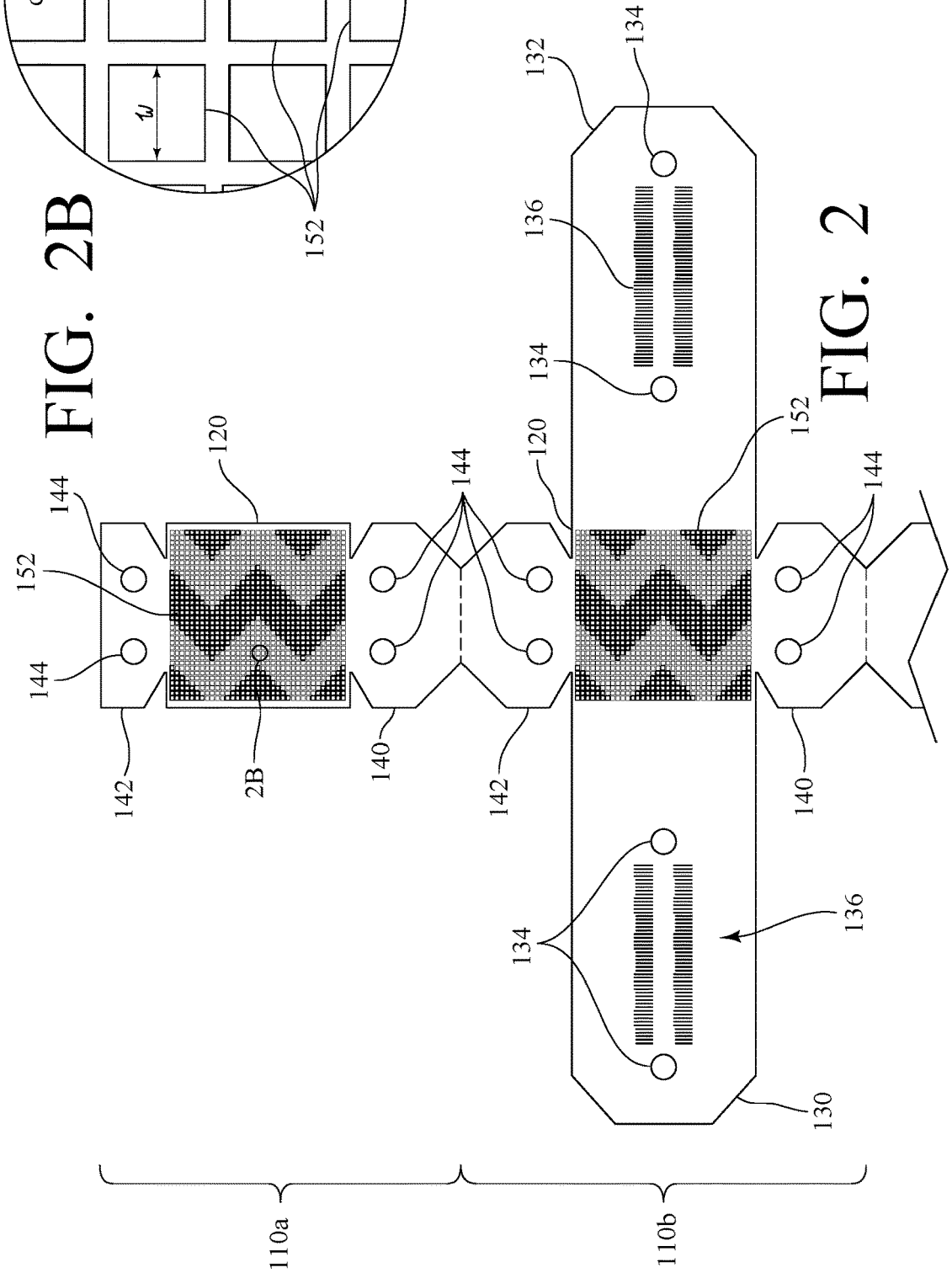
FIG. 2 is detailed view of two units of the flexible substrate of FIG. 1.

Referring now to FIGS. 2 and 2B, the central portion 120 of the first unit 110a includes a plurality of pads 152 which are arranged in an array and configured to connect to a high density ultrasound matrix array transducer. According to some embodiments, the plurality of pads 152 are arranged in a square array that is 30×30 (i.e., there are a total of 1024 pads), but the particular size and shape of the array of pads is determined by the size and shape of the related transducer array. For example, in some embodiments, there are at least fifty pads in the smallest dimension. Likewise, rectilinear, circular, and random arrangements of the pads are also contemplated.

Referring now specifically to FIG. 2B, the pads 152 themselves are also square having a width, w, and a length, l, of about 150 μm, but the particular size and shape of the pads 152 is also not limited. For example, the pads 152 shown in FIG. 7 are illustrated as substantially circular.

Referring still to FIG. 2B, the spacing, or pitch, of the pads 152 can also vary, but in some embodiments, the pitch of the pads 152 is between about 20 μm to about 500 μm in each direction. That is to say, the distance $d_1$ and the distance $d_2$ shown in FIG. 2B are each between about 20 μm to about 500 μm. In some preferred embodiments, the distance $d_1$ and the distance $d_2$ shown in FIG. 2B are each between about 100 μm to about 400 μm, between about 200 μm to about 300 μm, or between about 200 μm to about 250 μm. In one particular exemplary embodiment, the distance $d_1$ and the distance $d_2$ shown in FIG. 2B are each about 240 μm. Of course, the distance $d_1$ and the distance $d_2$ shown in FIG. 2B need not be the same distance and pitches may vary for apodization purposes.

Referring once again to FIG. 2 in particular, with reference to the second unit 110b, which is representative of each of the secondary units 110b-110e, the central portion 120 of the second unit 110b also includes a plurality of pads 152 similar to the first unit 110a. Although FIGS. 1 and 2, only show a first side of the substrate 100, as discussed further below and as shown in FIGS. 5-7, a second side of the substrate 100 opposite from the first side includes corresponding pads 154 located on the central portion 120 of each of the units 110a-110e with vias 156 connecting the pads 152 on the first side (i.e., first surface pads 152) to the pads 154 on the second side (i.e., second surface pads 154).

Referring still to FIG. 2, on each of the tabs 130, 132 of the second unit 110b there are a plurality of lands 136 which are mounting areas for affixing the additional electronic components 300, 400 shown in FIG. 5, and the electrical traces 182 shown in FIG. 5, but not illustrated in FIG. 2, electrically connect specific pads 152, 154 to the lands 136 as discussed further below. Each of the tabs 130, 132 further defines alignment holes 134, and likewise, each of the hinge portions 140, 142 defines two alignment holes 144, the purpose of which will be described later.

Figure 3:
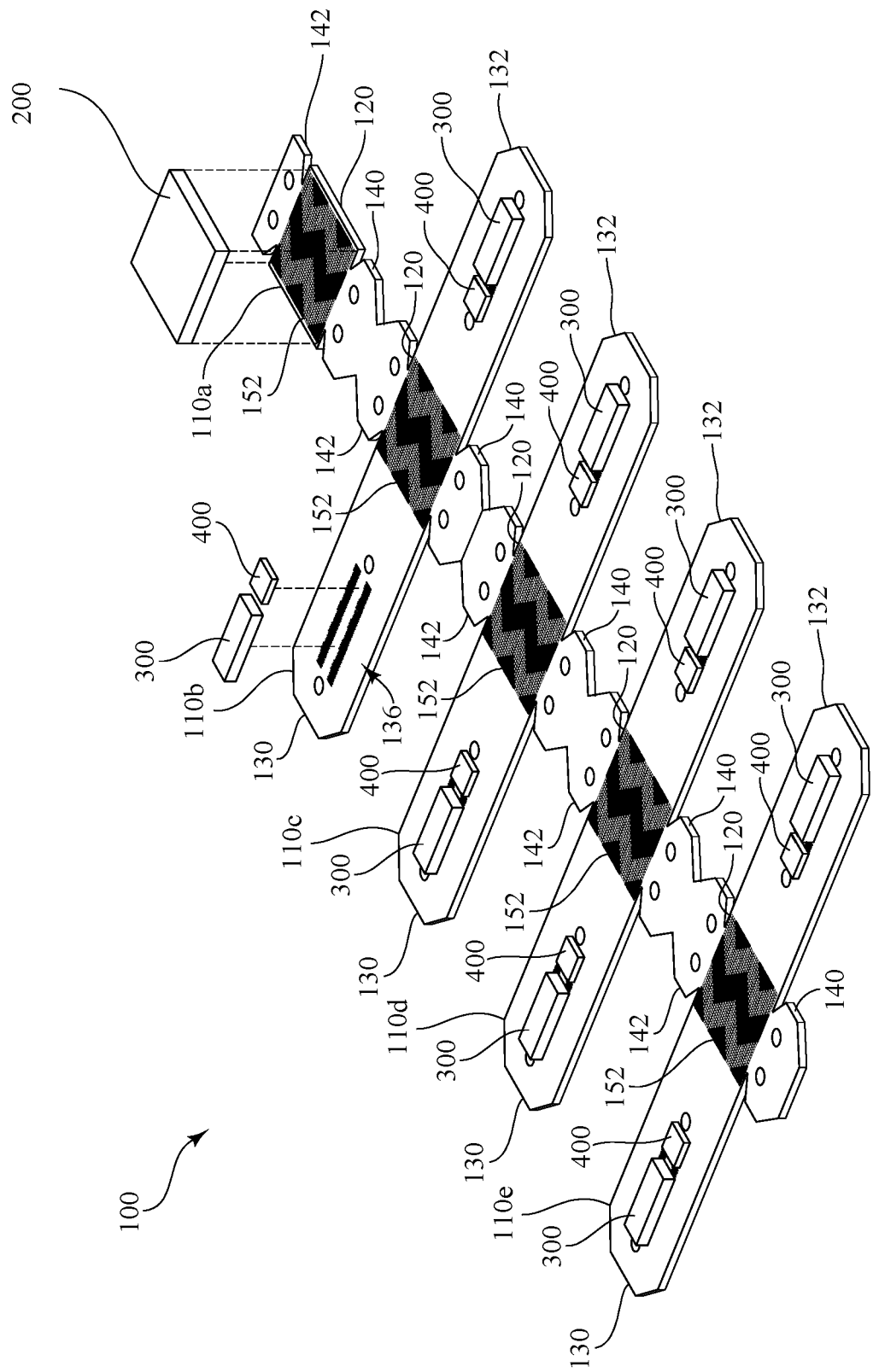
FIG. 3 is a perspective view of the flexible substrate of FIG. 1 illustrating a transducer and additional electronic components affixed to the substrate.

Referring now to FIG. 3, a transducer 200 is affixed to the pads 152 on the central portion 120 of the first unit 110a and additional electronic components are affixed to the lands 136 on each of the tabs 130, 132 of the subsequent units 110b-110e. More specifically, a connector 300 and an integrated circuit 400 are affixed to each of the tabs 130, 132 of the subsequent units 110b-110e, the purposes and operation of which is discussed further below. As show, it is preferably that every electronic component (e.g., transducer 200, connectors 300, and integrated circuits 400) is affixed to the substrate 100 prior to folding the substrate 100. To this end, prior to affixing the transducer 200 each of the pads 152 on the central portion 120 of the first unit 110a is covered using solder paste, solder balls, anisotropic conductive film (ACF), anisotropic conductive adhesive (ACA), or other such electrically conductive connective material known in the art. Each of the connectors 300 and integrated circuits 400 are likewise affixed to the relevant lands 136 by means known in the art. Furthermore, at least some of the pads 152 on the central portion 120 of each of the subsequent units 110b-110e are likewise covered with an electrically conductive connective material, as discussed further below.

The particular means of placing and affixing the electronic components to the substrate 100 is not limited, but in some preferred embodiments, a pick-and-place machine is utilized for high speed and precisions. Although in the exemplary embodiment each of the electronic components is affixed to the same side of the substrate 100, it is contemplated that placement on both sides of the substrate is possible. In such embodiments, after a first pick-and-place step on one side of the substrate is performed, the substrate is flipped upside down allowing a second pick-and-place step to occur on a second side of the substrate. In order to compensate for those electronic components already place on the first side of the substrate, a chuck is provided which includes cavities to accept those electronic components already attached and ensure that the substrate remains flat for the second pick-and-place step. During such a second pick-and-place steps, the electronic components attached should preferably not be placed in a position facing the electronic components attached during the first pick-and-place step.

Figure 4:
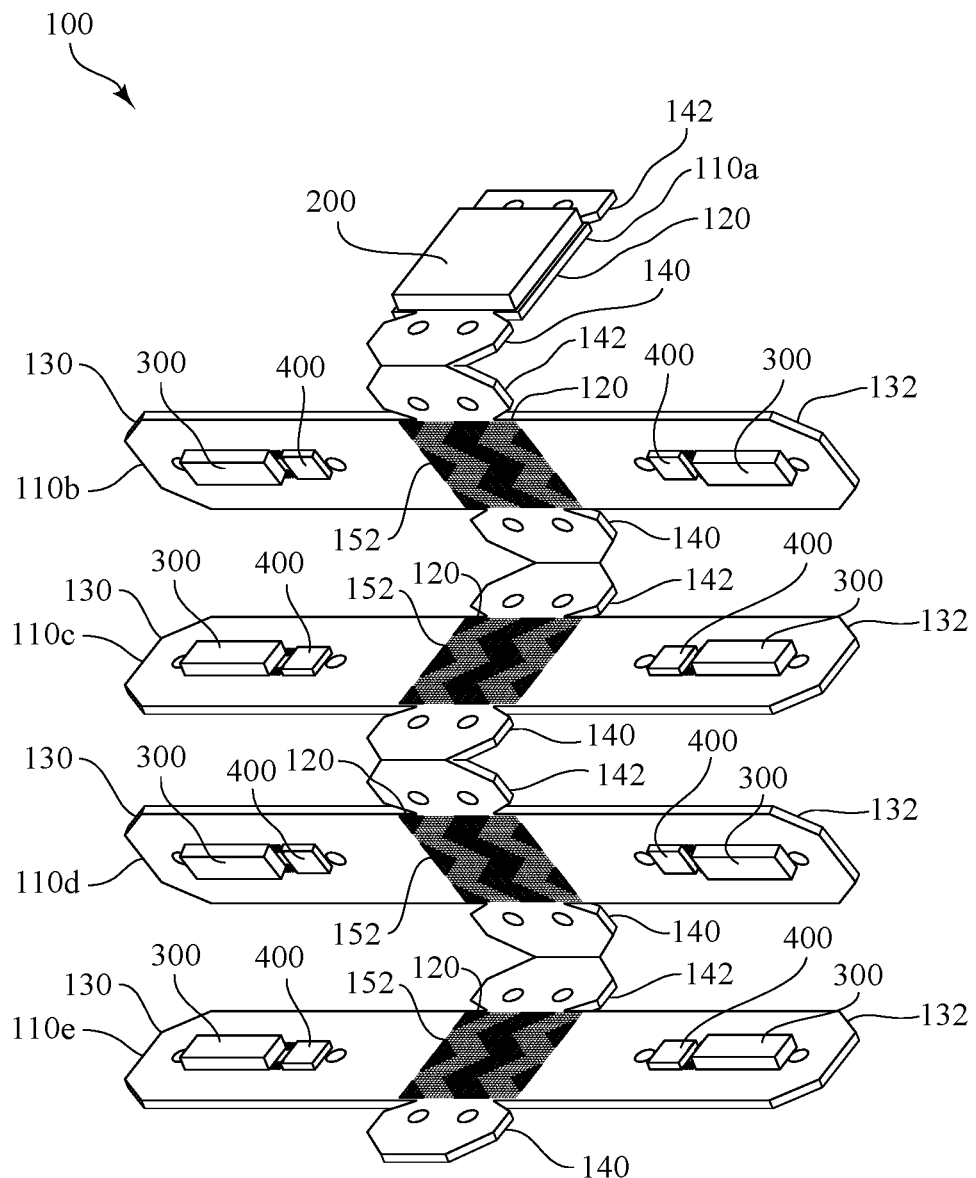
FIG. 4 illustrates how the flexible substrate of FIG. 3 is first folded such that the central portions of the substrate are vertically stacked.

Referring now to FIG. 4, having thus affixed each of the transducer 200, connectors 300, and integrated circuits 400, and applied an appropriate electrically conductive connective material to the pads 152 on the central portion 120 of each of the subsequent units 110b-110e, the substrate 100 is first folded between adjacent hinge portions 140, 142 such that the central portions 120 of all of the units 110a-110e are vertically stacked.

Due to the back and forth folding shown in FIG. 4, the substrate 100 is folded such that there are alternating pairs of the same surfaces facing one another. That is to say, and referring now specifically to FIG. 6, the first surface of the first unit 110a becomes an upper surface 112a of the uppermost, or first, circuit board 110a and the second surface of first unit 110a becomes a lower surface 114a of the first circuit board 110a; the second surface of second unit 110b becomes an upper surface 112b of the second circuit board 110b and the first surface of the second unit 110b becomes a lower surface 114b of the second circuit board 110b; the first surface of the third unit 110c becomes an upper surface 112c of the third circuit board 110c and the second surface of third unit 110c becomes a lower surface 114c of the third circuit board 110c; the second surface of fourth unit 110d becomes an upper surface 112d of the fourth circuit board 110d and the first surface of the fourth unit 110d becomes a lower surface 114d of the fourth circuit board 110d; and the first surface of the fifth unit 110e becomes an upper surface 112e of the fifth circuit board 110e and the second surface of fifth unit 110e becomes a lower surface 114e of the fifth circuit board 110e.

Accordingly, the second surface pads 154 of the first unit 110a are positioned above and directly connected with solder balls 158 to the second surface pads 154 of the second unit 110b; the first surface pads 152 of the second unit 110b are positioned above and directly connected with solder balls 158 to the first surface pads 152 of the third unit 110c; the second surface pads 154 of the third unit 110c are positioned above and directly connected with solder balls 158 to the second surface pads 154 of the fourth unit 110d; and the first surface pads 152 of the fourth unit 110d are positioned above and directly connected with solder balls 158 to the first surface pads 152 of the fifth unit 110e. Of course, rather than solder balls, other electrically conductive connective material (e.g., solder paste ACF, or ACA) can be used to connect the relevant pads. Furthermore, in some embodiments, direct pad to pad contact is utilized with non-conductive glue applied around the pads. In these embodiments, it is contemplated that the glue is applied on the whole surface of the flex and the glue is flushed from the pad surfaces by applying a pressure on the stack during the glue curing.

During this folding process, the alignment holes 144 defined within the hinge portions 140, 142 are used to ensure proper alignment of the central portions 120. Once folded, the central portions 120 of all of the units 110a-100e are interconnected as a multi-layer stack of circuit boards according to the interconnection media used (i.e., reflow for solder, hot bar process for ACF or ACA).

Next, each of the tabs 130, 132 are folded relative to the central portions 120, resulting in the electronics assembly 102 shown in FIG. 5. During this folding process, the alignment holes 134 defined within the tabs 130, 132 are used to ensure proper alignment of tabs 130, 132. As shown in FIG. 5, when the substrate 100 is thus folded, the connectors 300 of adjacent tabs 130, 132 face each other. Accordingly, in some preferred embodiments, the substrate includes an odd number of units with the first unit not including any tabs and each subsequent unit including tabs. In this way, upon folding the substrate, the connectors for each pair of units face each other can be easily affixed to both faces of a printed circuit board (PCB) (not shown) for electronic communication with other equipment, as discussed further below.

In order to reduce the lateral dimensions of the electronic assembly 102, it is preferable that the tabs 130, 132 are folded at about a 90° angle. To this end, it is contemplated that in some preferred embodiments, the central portion 120 of each of the units 110a-110e is formed such that when the tabs 130, 132 are folded, there is enough room between the tabs 130, 132 to accommodate the relevant electronic components (e.g., connectors 300 and/or integrated circuits 400) positioned between the folded tabs 130, 132 as shown in FIG. 5.

Referring now to FIGS. 5-7, electrical traces 182 connect the plurality of pads 152, 154 located in the central portion 120 of each unit 110b-110e to the lands 136 located in each of the respective tabs 130, 132 of the unit 110b-110e. In this way, the routing flexibility is increased allowing for a greater number of elements of the transducer 200 to be in electrical communication with the connectors 300 and integrated circuits 400. Of course, additional vias 184 (shown in FIG. 5) formed through the tabs 130, 132 are then required to eventually route all of the traces to the land 136. Of note, for reliability reasons it is considered preferable that none of the vias 156, 184 are place in the immediate vicinity of any of the folding areas.

Referring now to FIGS. 5-6, as previously mentioned, the pads 152, 154 of each of the stacked central portions 120 are interconnected. However, for each of the units, only certain of the first surface pads 152 are connected to the second surface pads 154 by way of vias 156. Furthermore, traces 182 extend away only from certain of the first surface pads 152 and/or the second surface pads 154 of each of the units 110b-110e and to respective lands 136. For example, and referring now to FIG. 7, on the second unit 110b, only the two outermost rows of pads 152 have traces 182 that extend away from the pads 152. On the third unit 110c, the next two rows of pads 152 have traces 182 that extend away from the pads 152. The two central rows of pads 152 have no traces on the second unit 110b or the third unit 110c but instead include vias 156 which extend through each of the first unit 110a and the second unit 110b. As previously mentioned, and as perhaps best shown in FIGS. 5 and 6, vias 156 are used only when it is desired to route signals for a specific transducer element to a lower stacked layer and to an attached trace. In this way, each of the elements of the transducer is connected to a specific integrated circuit 400 and each of the integrated circuits 400 are thereby in electrical communication with a specific group of elements of the transducer 200. Each connector 300 is then in communication with a specific integrated circuit 400 to allow electrical signals to pass between the integrated circuit 400 and an external system through wires or the like (not shown).

Referring still to FIG. 7, in some instances spacers 160 are used in the place of pads where there is no electrical connection from one side of the substrate to the other. The spacers 160 are configured to match the height of the pads 152, 154 located elsewhere on the central portion 120. Without this height compensation, the stack height would vary across the central portions 120 which could result in issues if pressure is used during the connection process (e.g., applying a pressure on the stack during the glue curing) as the pressure will not be the same across the entire central portion 120 of the stack.

Once the stack is formed and interconnected, the hinge portions 140, 142 can be cut away from the central portions 120 along the cutting line L shown in FIG. 7.

Turning now specifically to the electronic components affixed to the substrate 100, although the transducer 200 shown in FIGS. 3-7 is illustrated as a single unit, according to some embodiments of the present invention, after placement of the transducer 200, a dicing step is performed to separate the transducer elements, either at the full height of the transducer material or on a partial depth. This step, however, is optional and only considered necessary for piezoelectric transducers, as compared to CMUT or PMUT transducers. However, should a dicing step be performed, it is contemplated that it is preferable to perform this step prior to placing and affixing any of the other electronic components (e.g, connectors 300 and integrated circuits 400). Therefore if the dicing step fails, the additional electronic components are not added to a non-functional transducer.

With respect to the connectors 300, upon creating the electronics assembly 102 as described above, this electronics assembly 102 is affixed to a PCB (with extra electronic components) or to wires by way of the connectors 300. Of note, the wires are not necessarily directly inserted into the connector 300 affixed to the tabs 130, 132 but instead a second connector mounted on a small PCB is matched with the connector 300 affixed to the tabs 130, 132 to reroute the signals to pads on the PCB where the wires are soldered. The electronics assembly 102 is thereby integrated into an ultrasonic probe and these wires provide for communication to an external system including, for example, imaging equipment, displays, user controls, and the like.

With respect to the integrated circuits 400, rather than relying on a direct communication between an external system and each element of the transducer 200 via the connectors 300, each integrated circuit 400 allows for local control of a group of the elements the transducer 200. Communication between the external system and each of the integrated circuits 400 is then provided by the connectors 300. Inclusion of the integrated circuits 400 therefore provides a significant decrease in the number of connections to the external system.

Although in the embodiment described above, both connectors 300 and integrated circuits 400 are affixed to each of the tabs 130, 132, in some embodiments, the connectors alone are used to directly pass electrical signals between each of the elements of the transducer and an external system. Of course, any combination of connectors and integrated circuits is possible. Furthermore, other electronic components could also be included on the electronics assembly of the present invention without departing from the spirit and scope of the present invention.

As discussed above, in the exemplary substrate 100 used in forming the electronics package 102, the central portions 120 of the multiple units 110a-110e are linearly aligned such that folding of the hinge portions 142, 144 occurs along a single direction. In other embodiments of the present invention, however, and referring now to FIGS. 8-11, multi-directional folding is contemplated.

Figure 8:
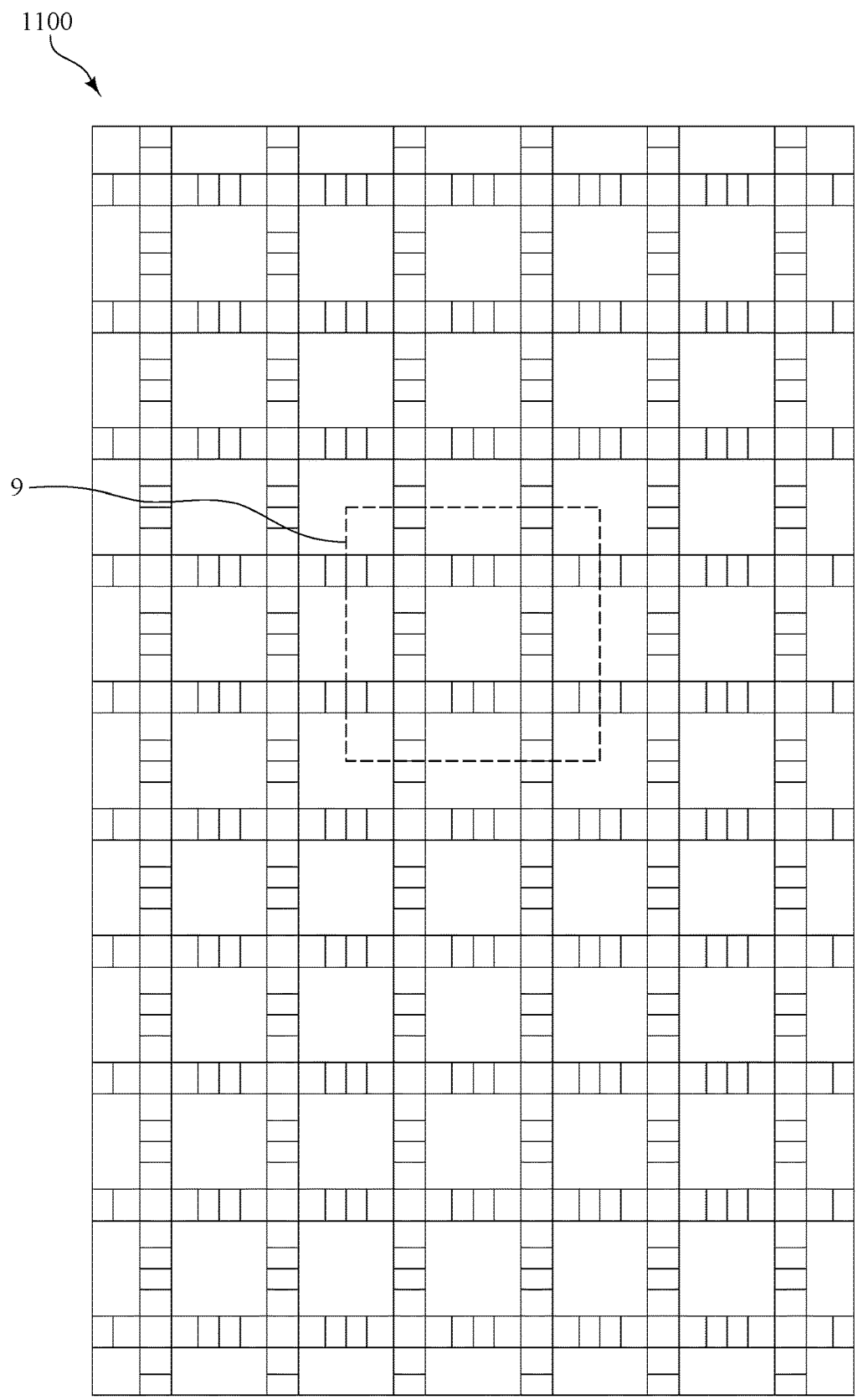
FIG. 8 is a plan view of a flexible substrate made in accordance with a second embodiment of the present invention.
Figure 9:
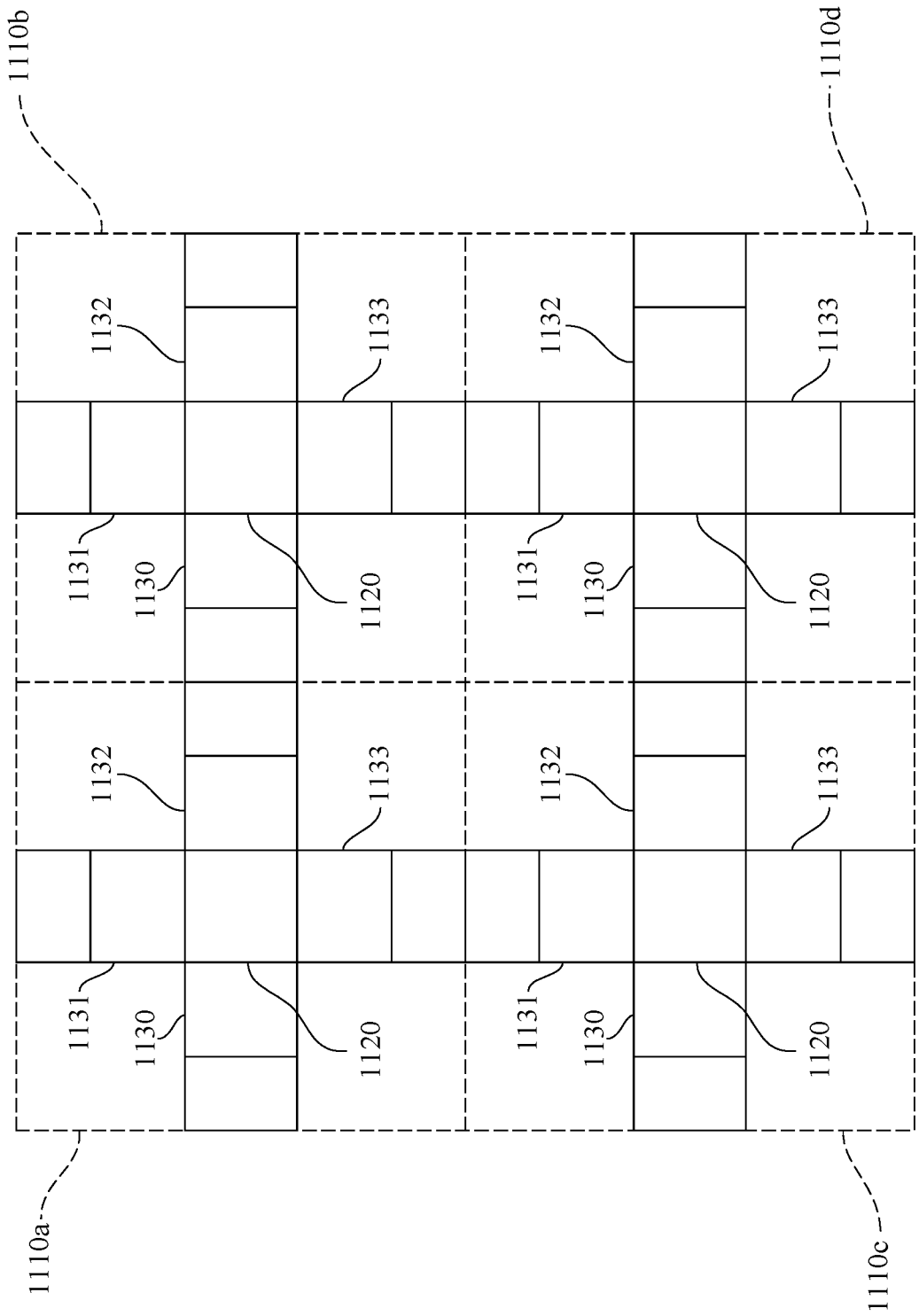
FIG. 9 is detailed view of four units of the flexible substrate outlined in FIG. 8.
Figure 10:
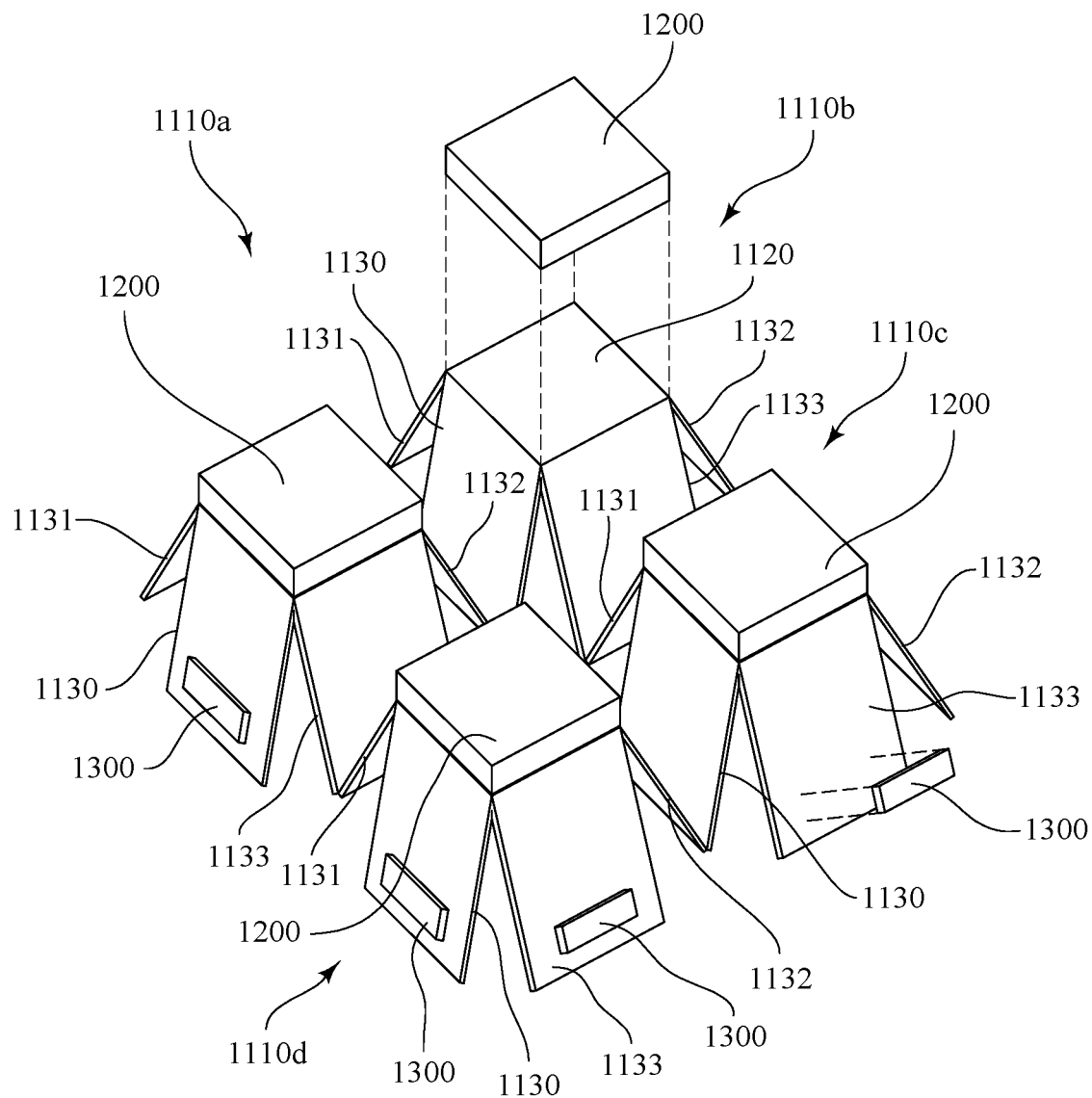
FIG. 10 illustrates how the four units of the flexible substrate of FIG. 9 are folded after transducers and additional electronic components are affixed to the substrate.

Referring now specifically to FIG. 8, a flexible substrate 1100 is provided which includes a plurality of units which are connected together in a grid arrangement. More specifically, as shown in FIG. 9, which illustrates four such units 1110a-1110d which are representative of all of the units in the flexible substrate 1100, each unit 1110a-1110d includes a central portion 1120 with four tabs 1130, 1131, 1132, 1133 extending away from the central portion 1120 and which are configured to fold relative to the central portion 1120, as illustrated in FIG. 10. It is contemplated that the central portions 1120 of the second embodiment are substantially similar to the central portions 120 of the first embodiment and the tabs 1130, 1131, 1132, 1133 are substantially similar to the tabs 130, 132 of the first embodiment except as noted otherwise. That is to say, although not expressly discussed with respect to FIGS. 8-11, a person of ordinary skill would readily understand how to form pads, vias, traces, and lands on the flexibles substrate 1100 to operate in a similar manner as in the first embodiment to electrically connect transducers to additional electronic components, as discussed below. Likewise, alignment holes can be included to facilitate in the folding processes.

Similar to the first embodiment, as shown in FIG. 10, prior to folding the flexible substrate 1100, a transducer 1200 is affixed to the central portion 1120 and additional electronic components (e.g., a connector 1300) is affixed to one or more of the tabs 1130, 1131, 1132, 1133. Although only connectors 1300 are illustrated in the second embodiment, integrated circuits or any other electronic components could also be included as discussed above with respect to the first embodiment.

Figure 11:
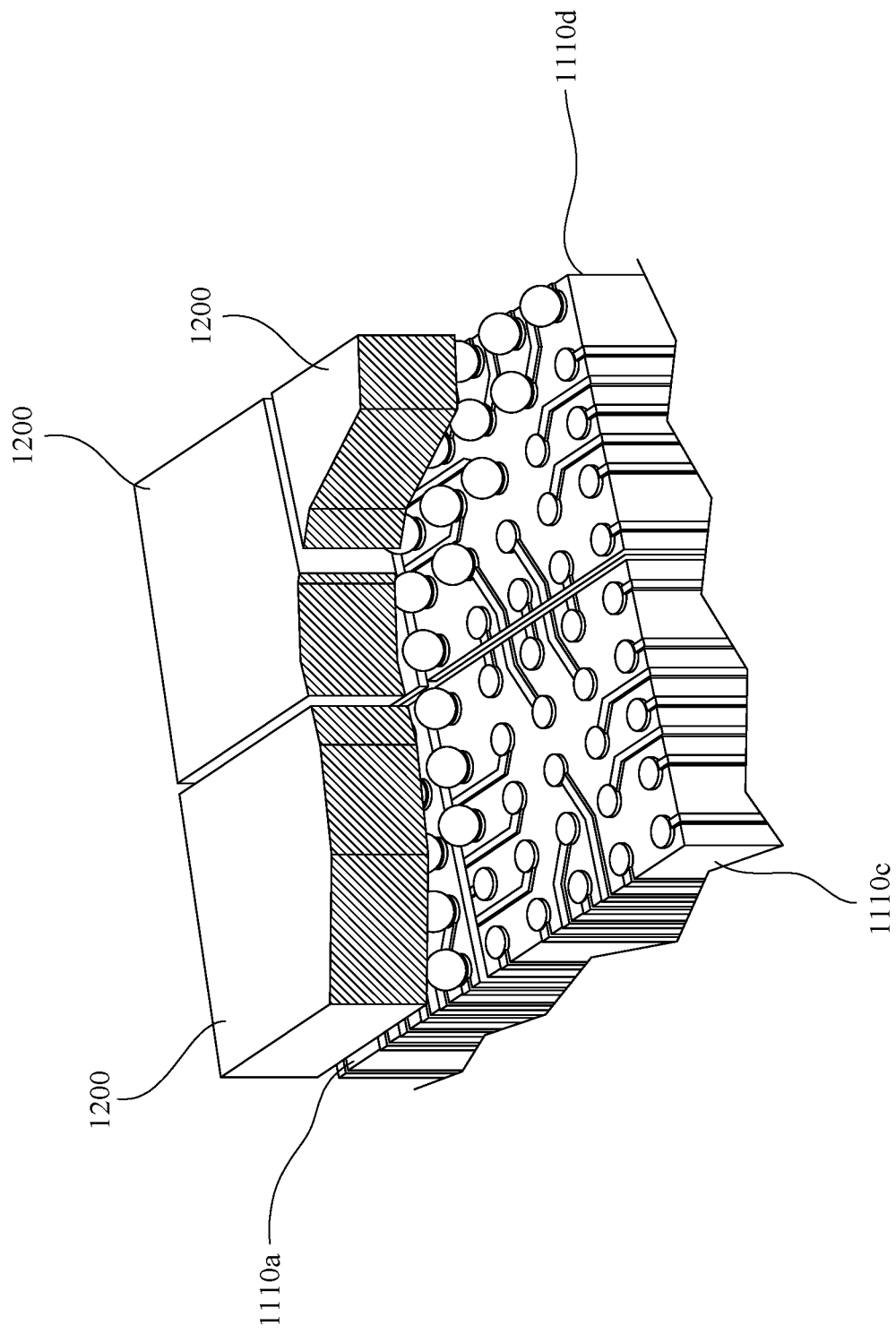
FIG. 11 is a partial cutaway of a perspective view of an electronics assembly made in accordance with the second embodiment of the present invention.

Referring now to FIG. 11, unlike the first embodiment, there are no hinge portion and thus the folding occurs between each of the tabs 1130, 1131, 1132, 1133 and the central portion 1120. In this way, the tabs 1130, 1131, 1132, 1133 of the second embodiment act similar to the hinge portion 142, 144 of the first embodiment.

Once the folding is completed, four transducers 1200 are positioned immediately adjacent to one another. It is contemplated that these adjacent transducers 1200 can collectively operate as a multiple acoustic component.

Referring still to FIG. 11, the central portions 1120 are not vertically stacked, but are, instead, positioned adjacent to each other within the same plane. As such, it is not possible to route signals for a specific transducer element to a lower stacked layer. However, the inclusion of four tabs 1130, 1131, 1132, 1133 surrounding each central portion 1120 in the second embodiment provides for additional locations where electronics (e.g., connectors 1300) can be included. As such, there is still an improvement in the overall compactness of the electronics assembly.

In the second embodiment shown in FIGS. 8-11, a square architecture is utilized, but it is contemplated that other arrangements are possible with corresponding folding patterns including, but not limited to triangular or spiral folding.

Furthermore, although only four central portions are illustrated fold together in FIGS. 9-11, it is contemplated that the flexible substrate 1100 could be folded such that any number of central portions are positioned adjacent to one another. The overall size and shape of the resulting multiple acoustic component formed after folding is therefore not limited to a 2×2 square of four transducers. Depending on the particular size and shape desired of the resulting structure, the necessary units are cut from the substrate 1100 prior to folding.

One of ordinary skill in the art will recognize that additional embodiments are possible without departing from the teachings of the present invention. This detailed description, and particularly the specific details of the exemplary embodiment disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A flexible printed circuit board comprising:
   a plurality of central portions positioned along a first direction;
   hinge portions extending between adjacent central portions, each hinge portion foldable;
   one or more tabs extending from each of the plurality of central portions in a second direction perpendicular to the first direction, the one or more tabs foldable relative to the central portion from which the one or more tabs extend;
   a plurality of first surface pads located within each of the plurality of central portions;
   a plurality of second surface pads located within each of the plurality of central portions on a side opposite from the plurality of first surface pads;
   vias extending through each of the plurality of central portions, each via electrically connecting one of the plurality of first surface pads to one of the plurality of second surface pads;
   lands located within one of the one or more tabs; and
   electrical traces connecting the plurality of first surface pads and the lands;
   wherein upon folding the flexible printed circuit board at the hinge portions, adjacent central portions can be vertically stacked and electrically connected by the plurality of first surface pads and plurality of second surface pads;
   wherein the plurality of first surface pads of one of the plurality of central portions is configured to electrically connect to a transducer.

2. The flexible printed circuit board of claim 1, further comprising a connector affixed to the lands, the connector configured to electronically communicate with imaging equipment.

3. The flexible printed circuit board of claim 1, further comprising an integrated circuit affixed to the lands, the integrated circuit configured to control one or more elements of the transducer.

4. The flexible printed circuit board of claim 1, wherein the one or more tabs extend from a periphery of each of the plurality of central portions.

5. The flexible printed circuit board of claim 1, wherein the plurality of second surface pads are configured to electrically connect to another flexible printed circuit board.

6. The flexible printed circuit board of claim 1, wherein the one or more tabs define alignment holes extending through tabs.

7. The flexible printed circuit board of claim 1, wherein the hinge portions define alignment holes extending through the hinge portions.

8. A flexible printed circuit board comprising:
   a plurality of central portions;
   one or more tabs extending from each of the plurality of central portions and between adjacent central portions, each of the one or more tabs foldable relative to the central portion from which the one or more tabs extend and such that, upon folding the flexible printed circuit board at the tabs, adjacent central portions can be positioned immediately adjacent to each other within the same plane;
   a plurality of pads located within each of the plurality of central portions;
   lands located within one of the one or more tabs;
   electrical traces connecting the plurality of pads and the lands;
   wherein the pads of adjacent central portions collectively connect to a high density ultrasound matrix array transducer.

9. A method of manufacturing an electronics assembly, the method comprising the steps of:
   providing a flexible folding substrate having a first surface and a second surface opposite the first surface, the substrate including
      a plurality of central portions,
      hinge portions extending between adjacent central portions, and
      one or more tabs extending from each of the plurality of central portions,
      a plurality of pads positioned on the first surface of the substrate and on the second surface of the substrate, each pad located within one of the plurality of central portions of the substrate,
      vias extending through the substrate and electrically connecting one of the plurality of pads positioned on the first surface of the substrate to one of the plurality of pads positioned on the second surface of the substrate,
      lands positioned on the first surface of the substrate, each land located within one of the one or more tabs of the substrate, and electrical traces connecting the plurality of pads and the lands;

folding the substrate at each hinge portion such that the adjacent central portions are vertically stacked and the pads of adjacent central portions are electrically connected; and folding each of the tabs relative to the central portion from which the one or more tabs extend.

10. The method of claim 9 and further comprising a step of affixing a transducer to the plurality of pads positioned on the first surface of the substrate such that the transducer is affixed to an uppermost of the plurality of central portions after the substrate is folded at each hinge portion.

11. The method of claim 10, wherein the transducer is affixed to the plurality of pads prior to folding the substrate.

12. The method of claim 10, wherein the step of affixing the transducer comprises electrically connecting each element of a high density ultrasound matrix array transducer to a corresponding one of the plurality of pads positioned on the first surface of the substrate located within the uppermost of the plurality of central portions.

13. The method of claim 9 and further comprising a step of affixing one or more integrated circuits to the lands.

14. The method of claim 13, wherein the one or more integrated circuits are affixed to the lands prior to folding the substrate.

15. The method of claim 9, wherein the hinge portions define alignment holes extending through the substrate; and wherein the step of folding the substrate at each hinge portion includes aligning each of the alignment holes.

16. The method of claim 9, wherein the one or more tabs define alignment holes extending through the substrate; and wherein the step of folding each of the tabs includes aligning each of the alignment holes.

17. The method of claim 9 and further comprising a step of applying an electrically conductive connective material to the pads prior to folding the substrate.

18. The method of claim 17, wherein the electrically conductive connective material is solder and the method further comprises a step of heating the flex folding substrate to reflow the solder.

19. The method of claim 17, wherein the electrically conductive connective material is an anisotropic conductive film and the method further comprises a step of applying pressure to the vertically stacked plurality of central portions.

20. The method of claim 9 and further comprising a step of cutting away the hinge portions from each of the plurality of central portions after the pads of adjacent central portions are electrically connected.

21. The flexible printed circuit board of claim 1, wherein the plurality of first surface pads located on an uppermost of the plurality of central portions directly connects to the transducer and the plurality of first surface pads located on other of the plurality of central portions electrically connect to the plurality of first surface pads located on adjacent central portions.

* * * * *